(12) United States Patent
Schmidt et al.

(10) Patent No.: US 6,452,061 B1
(45) Date of Patent: Sep. 17, 2002

(54) CATALYTIC OXIDATIVE DEHYDROGENATION PROCESS

(75) Inventors: Lanny D. Schmidt, Minneapolis; Marylin Huff, St. Paul, both of MN (US)

(73) Assignee: Regents of the University of Minnesota, Minneapolis, MN (US)

(*) Notice: Subject to any disclaimer, the term of this patent is extended or adjusted under 35 U.S.C. 154(b) by 1522 days.

(21) Appl. No.: 08/636,816

(22) Filed: Apr. 23, 1996

Related U.S. Application Data

(63) Continuation of application No. 08/330,201, filed on Oct. 27, 1994, now abandoned.

(51) Int. Cl.[7] ................................................. C07C 5/48
(52) U.S. Cl. ...................................... 585/658; 585/660
(58) Field of Search .............................. 585/658, 660

(56) References Cited

U.S. PATENT DOCUMENTS

| | | | |
|---|---|---|---|
| 3,562,797 A | 2/1971 | Hu .......................... 260/683.3 |
| 4,767,569 A | 8/1988 | Brophy et al. .............. 252/373 |
| 4,810,685 A | 3/1989 | Twigg et al. ................. 502/60 |
| 4,827,071 A | * 5/1989 | Hazbun ...................... 585/443 |
| 4,902,849 A | 2/1990 | McKay et al. .............. 585/660 |
| 4,940,826 A | 7/1990 | Freide et al. ................ 585/600 |
| 5,073,657 A | * 12/1991 | Warren ....................... 585/500 |
| 5,105,052 A | 4/1992 | Freide et al. ................ 585/651 |
| 5,382,741 A | 1/1995 | Astbury ...................... 585/652 |
| 5,593,935 A | * 1/1997 | Golunski et al. ........... 502/339 |

FOREIGN PATENT DOCUMENTS

| | | |
|---|---|---|
| EP | 0178853 | 4/1986 |
| EP | 0189282 | 7/1986 |
| EP | 0332289 | 2/1989 |

OTHER PUBLICATIONS

Huff, M & Schmidt, L.D. "Ethylene Formation by Oxidative Dehydrogenation of Ethane over Monoliths at Very Short Contact Times", abstract, Advance ACS Abstracts,, vol. 1, No. 8, Oct. 15, 1993.*

Huff & schmidt. Ethylene Formation by Oxidative Dehydrogenation of Ethane Over Monoliths at Very Short Contact Times. J. of Phys. Chem 97 pp. 11815–11822. Nov. 1993.

Matsuda, Koike, Kubo & Kikuchi. Dehydrogenation of Isobutane to Isobutene in a Palladium Membrane Reactor. App. Catal. A 96 1993.

* cited by examiner

Primary Examiner—Bekir L. Yildirim
(74) Attorney, Agent, or Firm—Mueting, Raasch and Gebhardt, P.A.

(57) ABSTRACT

A process for the production of a mono-olefin from a gaseous paraffinic hydrocarbon having at least two carbon atoms or mixtures thereof comprising reacting said hydrocarbons and molecular oxygen in the presence of a platinum catalyst. The catalyst consist essentially of platinum supported on alumina or zirconia monolith, preferably zirconia and more preferably in the absence of palladium, rhodium and gold.

14 Claims, 11 Drawing Sheets

CATALYTIC OXIDATIVE DEHYDROGENATION PROCESS

This application is a continuation, of application Ser. No. 08/330,201 filed Oct. 27, 1994 now abandoned.

This invention relates to a process for the dehydrogenation of dehydrogenatable hydrocarbons in the presence of a selective oxidation/dehydrogenation catalyst and an oxygen-containing gas. This invention was made with government support under grant number DE-FG02-88ER13878-A02 awarded by the Department of Energy. The government has certain rights in the invention.

BACKGROUND OF THE INVENTION

1. Field of the Invention

The dehydrogenation of hydrocarbons is an important commercial process. This is because of the great demand for dehydrogenated hydrocarbons as feedstocks for industrial processes. For example, dehydrogenated hydrocarbons are utilized in the manufacture of various products such as detergents, high octane gasolines, and pharmaceutical products among others. Plastics and synthetic rubbers are other products which may be produced through use of dehydrogenated hydrocarbons. One example of a specific dehydrogenation process is dehydrogenating isobutane to produce isobutene which may be etherified to produce gasoline octane improvers, polymerized to provide adhesive tackifying agents, viscosity-index additives and plastic antioxidants.

2. Related Art

Various reticulated ceramic structures are described in the art: U.S. Pat. No. 4,251,239 discloses fluted filter of porous ceramic having increased surface area; U.S. Pat. No. 4,568,595 discloses reticulated ceramic foams with a surface having a ceramic sintered coating closing off the cells; U.S. Pat No. 3,900,646 discloses ceramic foam with a nickel coating followed by platinum deposited in a vapor process; U.S. Pat. No. 3,957,685 discloses nickel or palladium coated on a negative image ceramic metal/ceramic or metal foam; U.S. Pat. No. 3,998,758 discloses ceramic foam with nickel, cobalt or copper deposited in two layers with the second layer reinforced with aluminum, magnesium or zinc; U.S. Pat. Nos. 4,810,685 and 4,863,712 disclose negative image reticulated foam coated with active material, such as, cobalt, nickel or molybdenum coating; U.S. Pat. No. 4,308,233 discloses a reticulated ceramic foam having an activated alumina coating and a noble metal coating useful as an exhaust gas catalyst; U.S. Pat. No. 4,253,302 discloses a foamed ceramic containing platinum/rhodium catalyst for exhaust gas catalyst; and U.S. Pat. No. 4,088,607 discloses a ceramic foam having an active aluminum oxide layer coated by a noble metal containing composition such as zinc oxide, platinum and palladium.

The supports employed in the present invention are generally of the type disclosed in U.S. Pat. No. 4,810,685 using the appropriate material for the matrix and are generally referred to in the art and herein as "monoliths".

The monoliths with various catalytic materials deposited thereon have also been employed for the production of synthesis gas (PCT WO 90/06279) and nitric acid (U.S. Pat. No. 5,217,939).

U.S. Pat. No. 4,940,826 (Freide, et al) discloses the oxidative dehydrogenation of gaseous paraffinic hydrocarbons having at least 2 carbon atoms or a mixture thereof by contacting the hydrocarbon with molecular oxygen containing gas over a supported platinum catalyst where the support is alumina such as gamma alumina spheres and monoliths such as cordierite or mullite. The desired products are the corresponding olefins.

SUMMARY OF THE INVENTION

Briefly the present invention is a process for the production of a mono-olefin from a gaseous paraffinic hydrocarbon having at least two carbon atoms or mixtures thereof comprising reacting said hydrocarbons and molecular oxygen in the presence of a platinum catalyst, preferably in the substantial absence of Pd, Rh and Au on a monolith support.

The composition of the ceramic support can be any oxide or combination of oxides that is stable at the high temperatures of operation, near 1000° C. The support material should have a low thermal expansion coefficient. The components of the oxide support should not phase separate at high temperatures since this may lead to loss of integrity. Components of the oxide support should not become volatile at the high reaction temperatures. Suitable oxide supports include the oxides of Al ($\alpha$-$Al_2O_3$), Zr, Ca, Mg, Hf, and Ti. Combinations of these can be produced to tailor the heat expansion coefficient to match the expansion coefficient of the reactor housing.

The structure and composition of the support material is of great importance. The support structure affects the flow patterns through the catalyst which in turn affects the transport to and from the catalyst surface and thus the effectiveness of the catalyst. The support structure should be macroporous with 30 to 80 pores per linear inch. The pores should yield a tortuous path for the reactants and products such as is found in foam ceramics. Straight channel extruded ceramic or metal monoliths yield suitable flow dynamics only if the pore size is very small with >80 pores per linear inch.

The preferred catalyst of the present invention consists essentially of platinum supported on a ceramic foam monolith, preferably on zirconia or $\alpha$-alumina, and more preferably on zirconia. The platinum should be deposited on the surface of the ceramic to a loading of 0.2 to 90 wt. %, preferably 2 to 10 wt. %, and more preferably in the absence of palladium, rhodium, and gold. It has been found that palladium causes the catalyst to coke up and deactivate very quickly and thus should be excluded in any amount that is detrimental to the effectiveness of the catalyst. Though rhodium does not lead to catalyst deactivation the product distribution is less favorable. The presence of gold leads to a less active catalyst.

Preferably the Pt is supported on an alpha-alumina or zirconia ceramic foam monolith with 30 to 80 pores per linear inch, 30 to 70% void fraction, created in such a way to yield a tortuous path for reactants. The Pt may be supported on a ceramic foam monolith comprised of any combination of alpha-alumina, zirconia, titania, magnesia, calcium oxide, or halfmium oxide such that the support is stable up to 1100° C. and does not undergo detrimental phase separation that leads to loss in catalyst integrity.

The catalyst may comprise platinum on the alumina or zirconia monolith support.

DETAILED DESCRIPTION OF PREFERRED EMBODIMENTS

Figure 1:
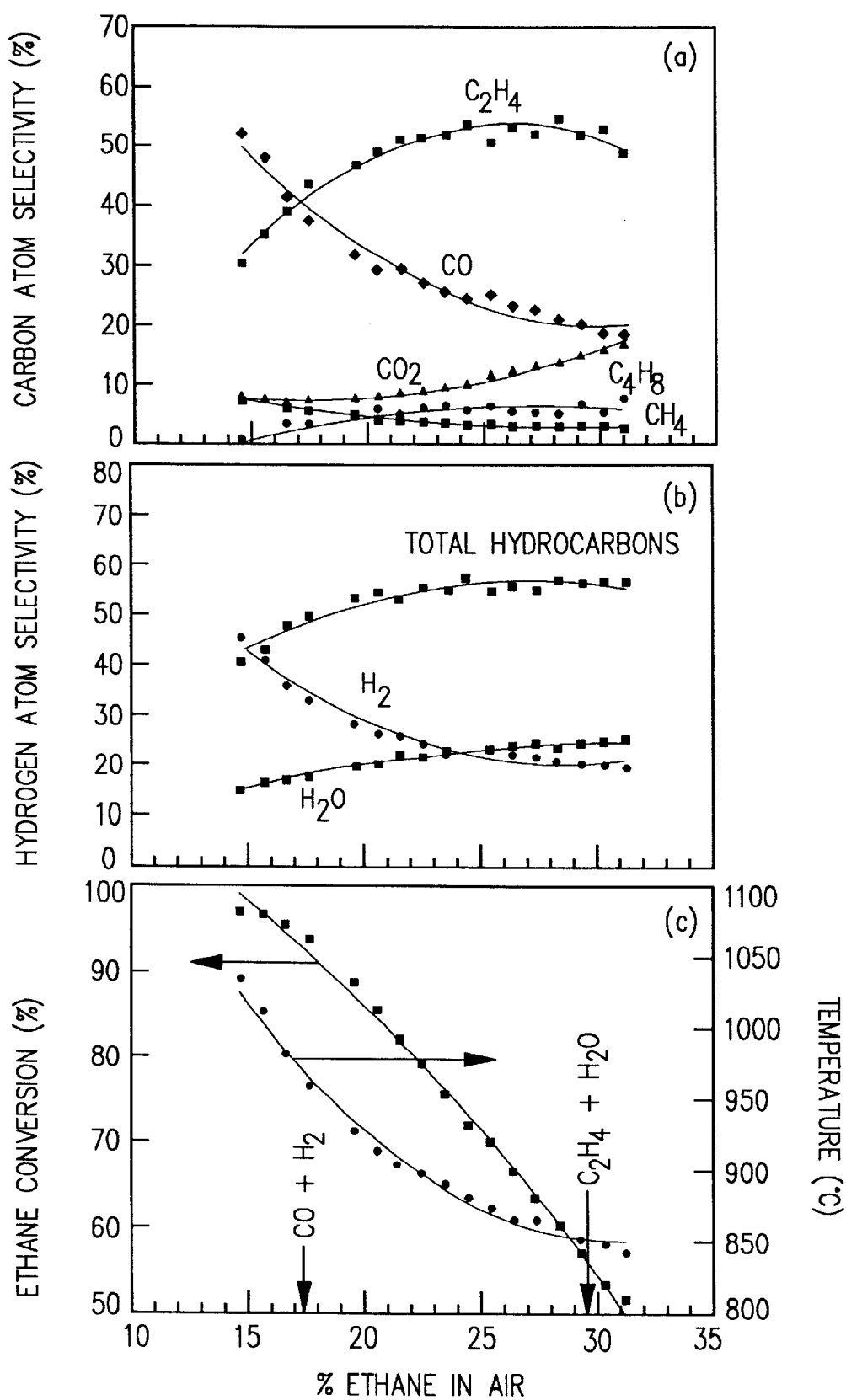
FIG. 1 shows the carbon atom and hydrogen atom selectivities, the ethane conversion, and the reaction temperature for feed mixtures of ethane and air as a function of feed composition.

The paraffins which are suitable for the present process are generally those that can be vaporized at temperatures in the range of 25 to 400° C. at pressures of 0.1 to 5 atm. These are generally $C_2$ to $C_{20}$ carbon atom alkanes either alone or in mixtures, preferably having two to eight carbon atoms. Suitable alkanes include ethane, propane, n-butane isobutane, n-pentane, isoamylenes, n-hexane, isohexanes, n-heptane, isoheptane, octane and isooctanes. Since a preferred embodiment includes a preheating of the feed to the reaction zone, the necessity to heat an alkane feed above ambient temperature to obtain a vaporous feed is not a negative consideration.

The feed may include both linear and branched alkanes. It has been observed in a fuel rich regime for the oxidative dehydrogenation of n-butane that the oxygen is completely consumed, whereas for the isobutane oxidations it is not. This oxygen breakthrough suggests a rate limiting step for isobutane. It is a proposed theory that the rates of these reactions should be related to the strengths of C—H bonds that must be broken. Thus, it may be desirable to preheat those feeds which are determined to have relatively strong C—H bonds to increase the rate of the initiation step. The feeds may be preheated to temperatures in the range of 0 to 500° C., preferably 25 to 400° C.

The present invention discloses the catalytic oxidative dehydrogenation of hydrocarbons. Mixtures of hydrocarbons and oxygen are flammable between given compositions. The feed compositions cited in this invention are outside the flammability limits for the cited hydrocarbons. In all cases, the feed compositions are on the fuel-rich side of the upper flammability limit. The compositions range from 2 to 16 times the stoichiometric fuel to oxygen ratios for combustion to $CO_2$ and $H_2O$. Some molar ratios are set out below in Table I.

TABLE I

| Fuel | Operable Fuel/ oxygen molar ratio | Preferred Fuel/ oxygen molar ratio |
| --- | --- | --- |
| Ethane | 0.8–2.5 | 1.5–2.0 |
| Propane | 0.5–1.5 | 0.8–1.3 |
| n-Butane | 0.45–1.0 | 0.6–0.8 |
| i-Butane | 0.45–2.25 | 1.4–2.1 |

As the diluent is reduced and as the reactants are preheated, the flammability limits widen, but it is under these conditions that higher fuel to oxygen ratios (farther from the flammable range) are preferred. This preference is based on catalyst performance with the extra measure of safety an added benefit.

Palladium cokes up rapidly when used alone in the present process. Thus palladium should be excluded in any amount that is detrimental to the effectiveness of the platinum in the dehydrogenation.

Rhodium is not a desirable catalyst component under the conditions of the present reaction since it tends to produce synthesis gas and not olefins. The term "synthesis gas" is understood to mean to a partial oxidation product comprising principally, in varying proportions of hydrogen, carbon monoxide and carbon dioxide. Thus rhodium should be excluded in any amount that is detrimental to the effectiveness of the platinum in the dehydrogenation.

Gold is less active than platinum. It has been found that catalysts prepared according to the present descriptions with gold alone or in combinations with platinum lack sufficient activity in the present process. Thus gold should not be present in the present catalyst in any amount which is detrimental to the activity of the platinum.

Under the conditions of the present process, olefin cracking, CO disproportionation and reverse steam reforming of carbon can occur, and may lead to coke formation. It has been found by varying the catalyst contact time, the amount of time allowed for these secondary reactions can be controlled. At higher flow rates the olefin products spend less time in contact with the catalyst and higher olefin selectivities and less coking are observed.

The present invention discloses the catalytic oxidative dehydrogenation of hydrocarbons in an autothermal reactor at millisecond contact time. High yields of mono-olefins are obtained with a catalyst contact time ranging from 0.1 to 20 milliseconds when using a ceramic foam monolith of 50% porosity and 0.2 to 1 cm in depth. Under operating conditions, this corresponds to GHSV of 60,000 to 3,000,000 $hr^{-1}$.

The flow rates are in the range of 60,000–10,000,000 $hr^{-1}$ GHSV, preferably in the range of 300,000 up to 3,000,000 $hr^{-1}$ GHSV may be used.

Under the conditions of the present process it can be determined that several reactions may occur namely (1) complete combustion (strongly exothermic); (2) partial oxidation to syngas (exothermic); (3) oxidative dehydrogenation (exothermic); (4) dehydrogenation (endothermic) and cracking (endothermic).

The overall process can be carried out autothermally. The heat produced by exothermic reactions provides the heat for endothermic reactions. The process does not require the addition of heat.

However, improved results are obtained when moderate amounts of heat are supplied to the system. Preheating the feed shifts the product distribution from the more exothermic reactions (combustion and partial oxidation) to the less exothermic (oxidative dehydrogenation) and endothermic (dehydrogenation and cracking) reactions. Since oxygen is the limiting reactant, this shift improves the process conversion. The selectivity is improved since the less exothermic and endothermic reactions are the desired reactions.

EXAMPLES

The reactor used in the following examples consisted of a quartz tube with an inside diameter of 18 mm containing the catalytic monolith which was sealed into the tube with high temperature alumina-silica cloth that prevented bypass of the reactant gases around the edges of the catalyst. To reduce radiation heat loss and better approximate adiabatic operation, the catalyst was immediately preceded and followed by inert alumina extruded monolith heat shields. The outside of the tube near the reaction zone was insulated.

The catalyst samples were prepared by impregnation of an $\alpha\text{-}Al_2O_3$ or $ZrO_2$ foam monolith disks 10 to 17 mm in diameter×0.2 to 1 cm long with saturated solution of metal salts. For the Pt catalysts, a saturated solution of $H_2PtCl_6$ in water was dripped onto a clean and dry $Al_2O_3$ foam monolith with 45 or 80 pores per inch (ppi) until the monolith was saturated with liquid. After the catalysts had been dried in $N_2$, they were calcined in air at 600° C. and then reduced in $H_2$. The Rh, Au and Pd catalysts were prepared similarly using saturated solutions of Rh acetylacetonate, gold chloride in water and Pd acetate in acetone. This process leads to 3–6 wt. % Pt loading for $\alpha\text{-}Al_2O_3$ and 1–2 wt. % Pt loading for $ZrO_2$ per impregnation step. Higher loadings were achieved by repeating this process.

The catalysts are prepared by depositing Pt or a mixture of Pt and Pd Rh or Au on commercially available ceramic foam monoliths. The foam monoliths, available from Hi-Tech Ceramics, Inc., are composed of either $\alpha\text{-}Al_2O_3$ or $ZrO_2$ with 30,45 or 80 pores per linear inch (ppi). It is important to note that these catalysts are not microporous structures. The monoliths are not wash-coated and are estimated to have a surface area of less than 70 $cm^2/g$. Suitable catalysts contain 0.2 to 20 wt % Pt.

Gas flow into the reactor was controlled by mass flow controllers which had an accuracy of ±0.1 slpm for all gases. The feed flow rates ranged from 2 to 12 slpm total flow, corresponding to 13 to 79 cm/s superficial velocity (i.e. the velocity of the feed gases upstream from the catalyst) at room temperature and atmospheric pressure. In all runs, the reactor pressure was maintained at 1.4 atm. The reaction temperature was ≈1000° C. and contact times were from 0.2 to 40 msec. Product gases were fed through heated stainless steel lines to an automated gas chromatograph.

For quantitative determination of concentrations, standards were used for all species except $H_2O$, which was obtained most reliably from an oxygen atom balance. To convert the product gas concentrations to molar quantities for a given feed basis, the mole number change due to the chemical reactions was calculated using the measured $N_2$ concentration. Since $N_2$ is an inert in this system, the ratio of product gas to feed gas moles was inversely proportional to the ratio of product gas $N_2$ concentration to feed gas $N_2$ concentration. Individual species concentrations were measured with a reproducibility estimated to be ±2%.

Temperatures were monitored using thermocouples inserted from the front and the rear of the quartz tube in one of the center channels of the inert monolith immediately before or after the catalytic monolith. The reactor was operated at a steady state temperature which is a function of the heat generated by the exothermic and endothermic reactions and the heat losses from the reactor.

The runs were carried out with either air or $O_2$ as the oxidant. In the runs using $O_2$, $N_2$ was typically added at 20% of the feed as an internal GC calibration standard.

Although the process in steady state is autothermal with feed gases at room temperature, heat was supplied initially to ignite the reaction. A mixture of hydrocarbon and air near the stoichiometric composition for production of synthesis gas was fed to the reactor, and the reactants were heated to the heterogeneous ignition temperature (≈230° C. for $C_2$ to $C_4$ hydrocarbons). After light-off, the external heat source was removed (unless feed preheating is indicated), the reaction parameters were adjusted to the desired conditions, and steady state was established (≈10 min) before analysis. Except where carbon deposition is noted, data shown were reproducible for time periods of at least several hours and on several catalyst samples.

Example 1

Ethane in Air

FIG. 1 shows the carbon atom and hydrogen atom selectivities, the ethane conversion, and the reaction temperature for feed mixtures of ethane and air as a function of feed composition. The feed composition was varied while maintaining a fixed total flow of 5 slpm with room temperature feed. Thermodynamics predicts that between 6 and 17%, selectivities should switch from $CO_2$ to CO and from $H_2O$ to $H_2$ and the temperature should be much lower, near 800° C. As seen in FIG. 1, at 17.4% $C_2H_6$ in air, 40% selectivity to ethylene at 950° C. is observed. This is extraordinary since thermodynamics predicts 100% conversion of ethane to CO and $H_2$ with no significant by-products.

In FIG. 1, $C_2H_4$ selectivity is seen to peak near a composition of 25% $C_2H_6$ in air ($C_2H_6/O_2$=1.7) with an optimal selectivity of 52% at 65% conversion of ethane. As the percentage of ethane in the feed increases beyond 25%, ethylene production remains high, but butene is also formed by dimerization of $C_2H_4$ thus decreasing the apparent C2H4 selectivity.

Example 2

Ethane in $O_2$

Figure 2:
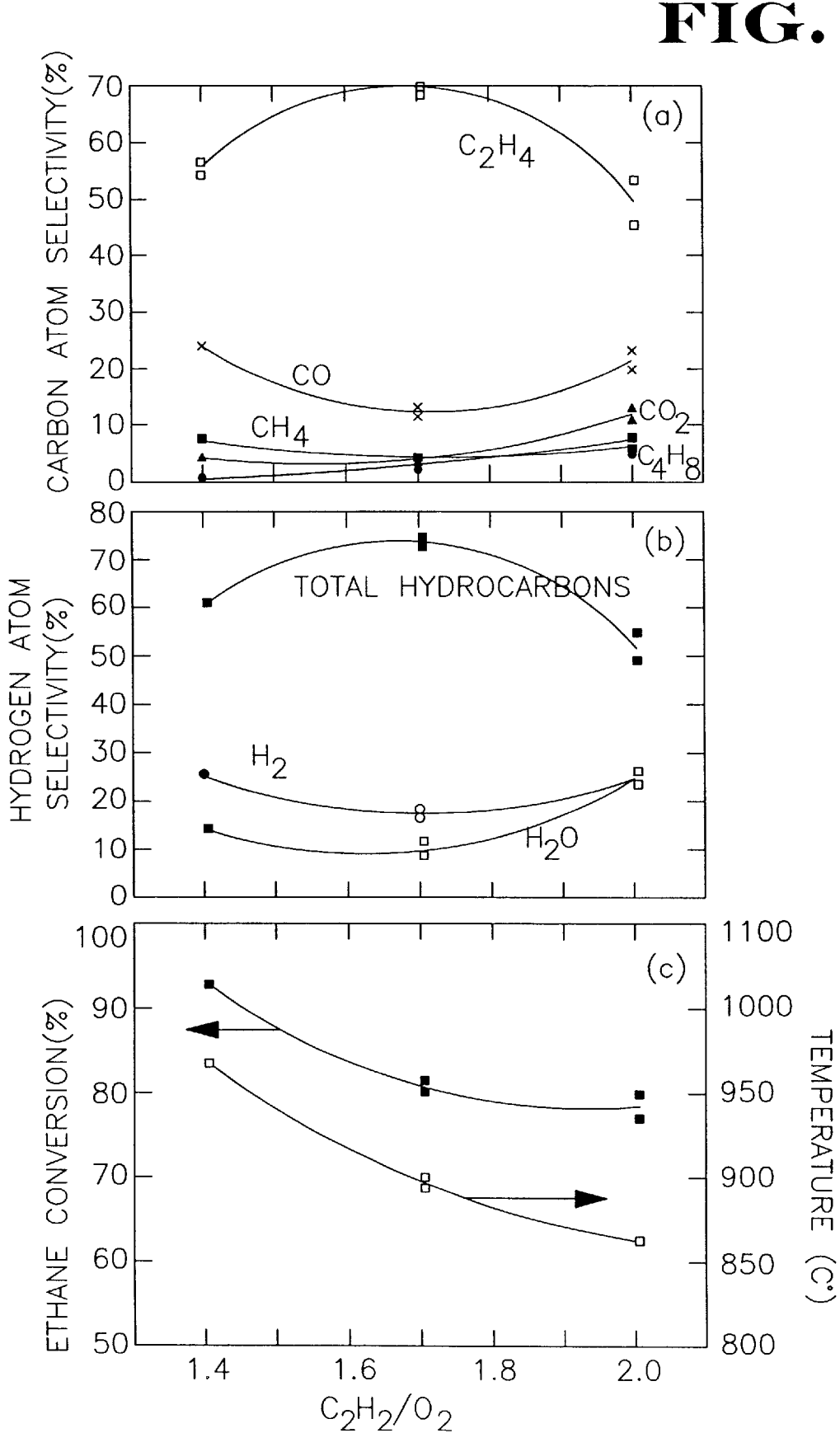
FIG. 2 shows the selectivities, conversion, and reaction temperature for ethane oxidation in $O_2$ as a function of feed composition.

FIG. 2 shows the selectivities, conversion, and reaction temperature for ethane oxidation in $O_2$ as a function of feed composition. The feed composition was varied while maintaining 20% $N_2$ in the stream and a fixed total flow of 4.5 slpm with room temperature feed.

The observed trends in the $O_2$ runs are similar to the trends observed in the air runs (FIG. 1). However, the selectivity to $C_2H_4$ and the $C_2H_6$ conversion are both significantly higher with 70% and 82%, respectively, at a $C_2H_6/O_2$ ratio of 1.7. The reaction temperature is also higher, illustrating the effect of reduced $N_2$ diluent.

Example 3

Preheat

Figure 3:
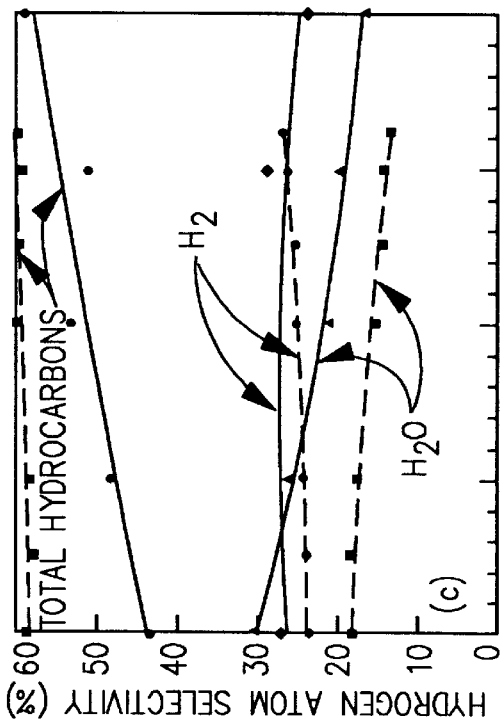
FIG. 3 illustrates the effect of preheat on the selectivities, conversion and reaction temperature in ethane oxidation.
Figure 3:
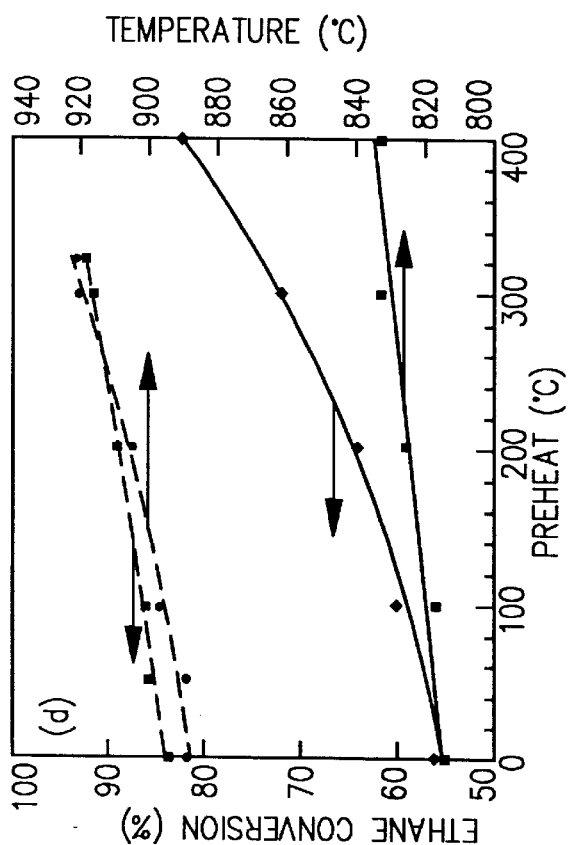
Figure 3:
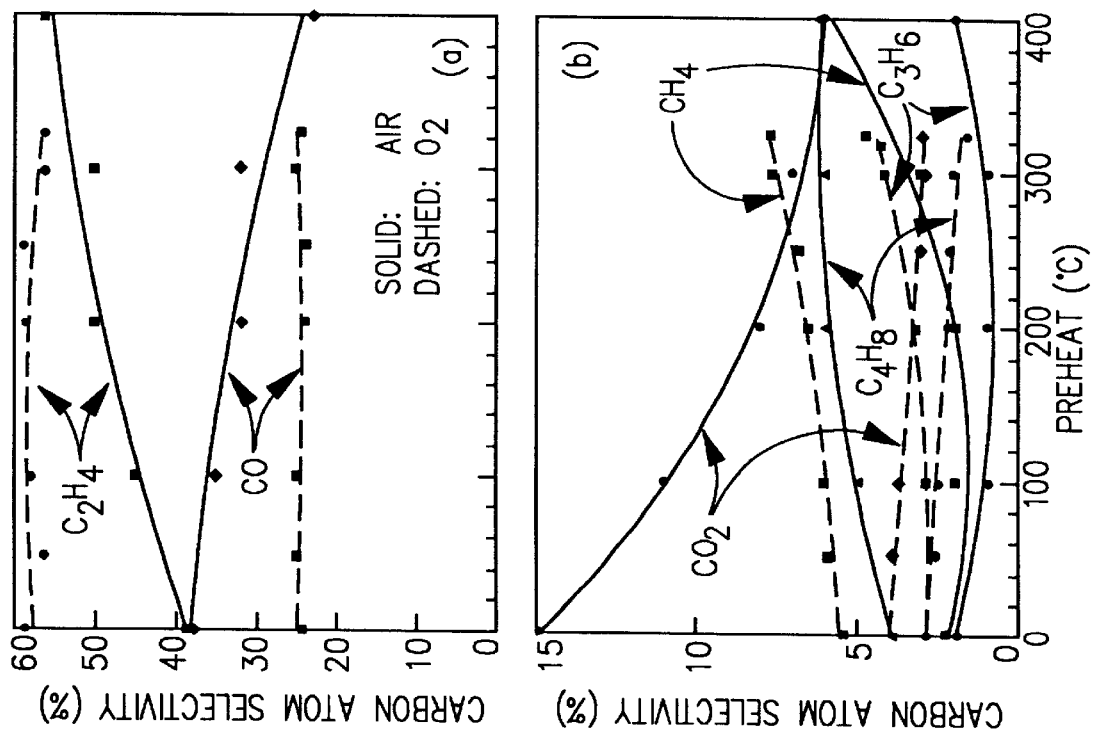

FIG. 3 illustrates the effect of preheat on the selectivities, conversion, and reaction temperature. The $C_2H_6/O_2$ ratio was 1.62. The total flow rate was 5 and 4 slpm for the air and $O_2$ runs, respectively. The ethylene selectivities presented here without preheat differ from the optimum shown in FIGS. 1 and 2 because the $C_2H_6/O_2$ ratio and flow rates were sub-optimum in this case.

For the air runs, preheat greatly influenced both the selectivities and the conversion. At 400° C. preheat $C_2H_4$ selectivity increased by 40% while the ethane conversion increased to over 80%. The addition of preheat raises the autothermal reaction temperature and provides heat for some endothermic reactions including thermal dehydrogenation of $C_2H_6$ which would otherwise require heat from the exothermic oxidation of ethane to CO and $H_2$. FIG. 3 shows that as preheat is increased, less CO and more $C_2H_4$ are formed. Hydrogen production remains virtually the same since $H_2$ is also a dehydrogenation product.

In the $O_2$ runs, increased ethane conversion was observed, but the selectivities remained nearly constant over the range of preheat used. It is important to note that the autothermal temperature is significantly higher in $O_2$ than in air.

Example 4

Flow Rate

Figure 4:
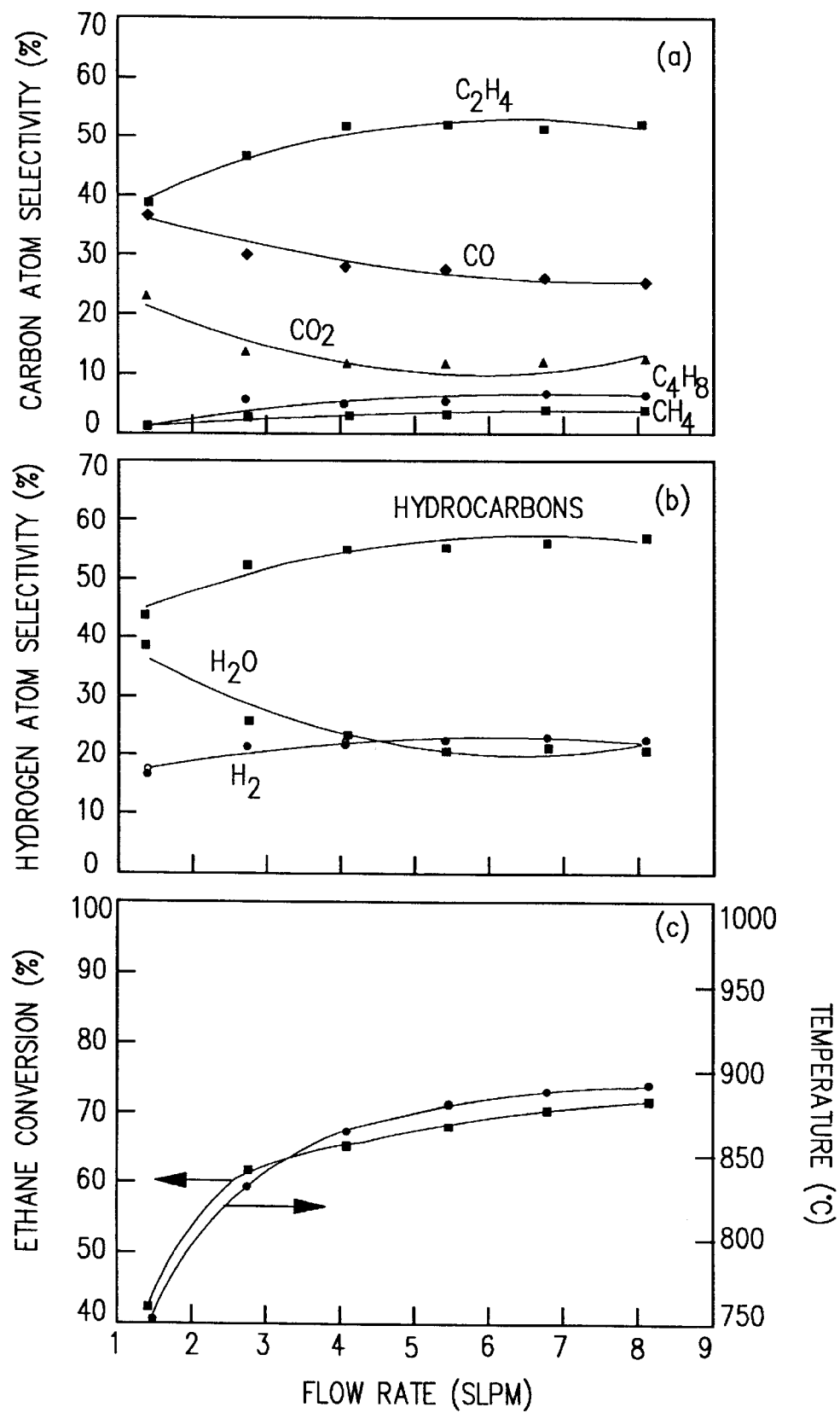
FIG. 4 illustrates the effect of flow rate on the selectivities, conversion, and reaction temperature for the same catalyst sample at a feed composition of 25% ethane in air.

FIG. 4 illustrates the effect of flow rate on the selectivities, conversion, and reaction temperature for the same catalyst sample at a feed composition of 25% $C_2H_6$ in air. It is seen that higher flow rates produce both greater $C_2H_4$ selectivities and greater ethane conversion. At low flows, significantly more $H_2O$ and $CO_2$, complete oxidation products are formed which consume the $O_2$ and thus decrease the conversion of ethane. The $H_2O$ production only drops slightly at the higher flows. No decrease in ethane conversion at flow rates up to 8 slpm corresponding to a contact time of ≈10 msec was observed.

Example 5

Rh

Figure 5:
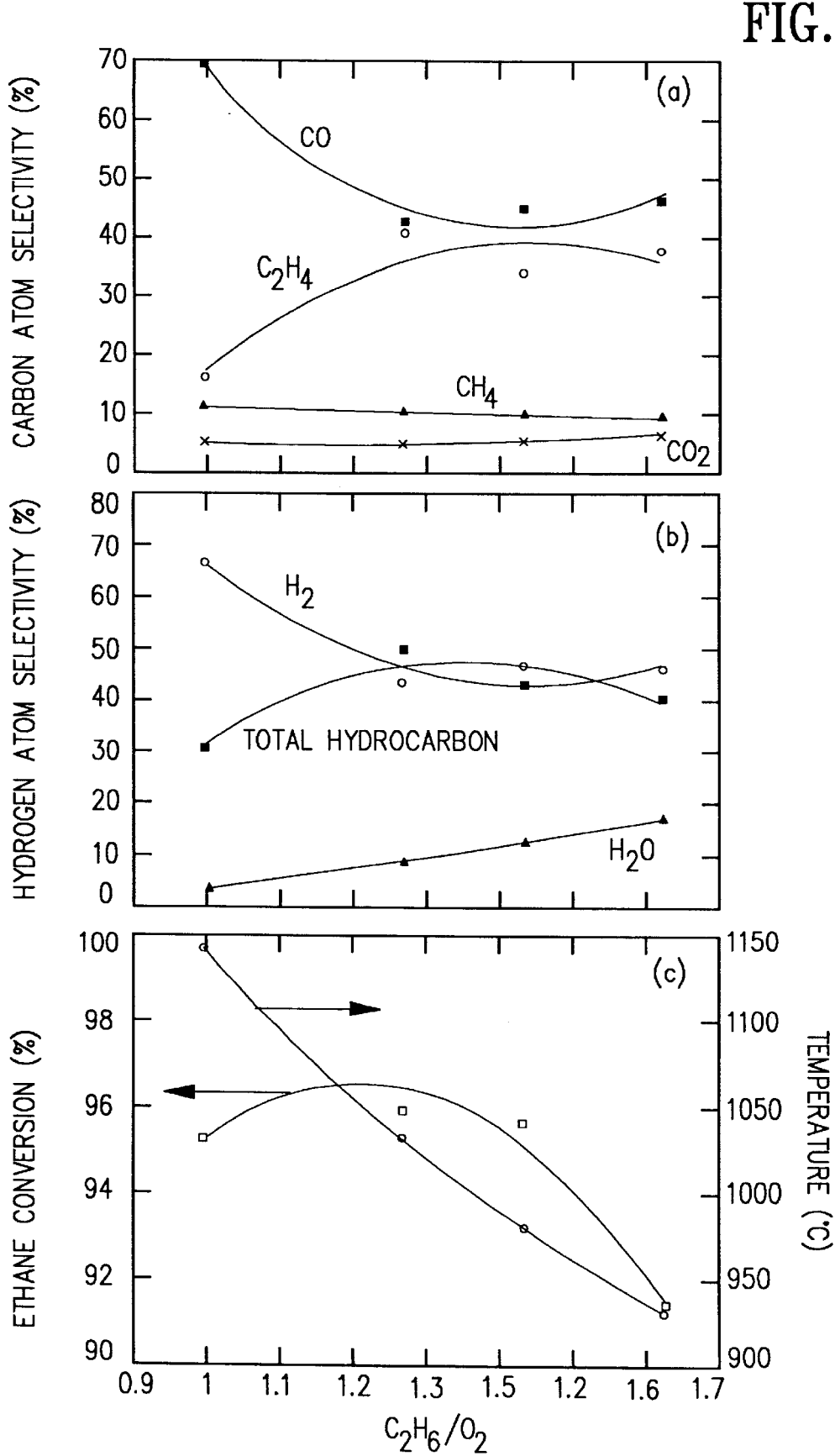
FIG. 5 shows the selectivities, conversion, and reaction temperature for ethane oxidation in $O_2$ over a Rh catalyst.

FIG. 5 shows the selectivities, conversion, and reaction temperature for ethane oxidation in $O_2$ over a 4 wt. % Rh catalyst as a function of feed composition at a fixed total flow of 5 slpm with room temperature feed. In contrast to the results shown in FIG. 2 for Pt, syngas production dominates on Rh. At a $C_2H_6:O_2$ ratio of 1.62 C2H4 selectivity is only 40% instead of nearly 70% for Pt. Also, significantly less $CO_2$ is formed as required by the oxygen balance.

Example 6

Pd

A run under the standard conditions was conducted using a 1.9 wt % Pd catalyst. Even at the ratio ($C_2H_6/O_2$=1.0), coke was forming rapidly. Within 20 minutes, the catalyst was completely deactivated and would not sustain reaction. The initial gas phase products, however, had 16% selectivity to $C_2H_4$ and 55% selectivity to CO at this feed composition. These are close to the values seen on the Pt catalyst at the syngas ratio, except carbon deposition does not occur on the Pt catalyst.

Example 7

In these runs for dehydrogenation of isobutane, comparisons of the monolith and platinum loading were made at two concentrations of isobutane. The conditions and results are set out in TABLE II.

Figure 10:
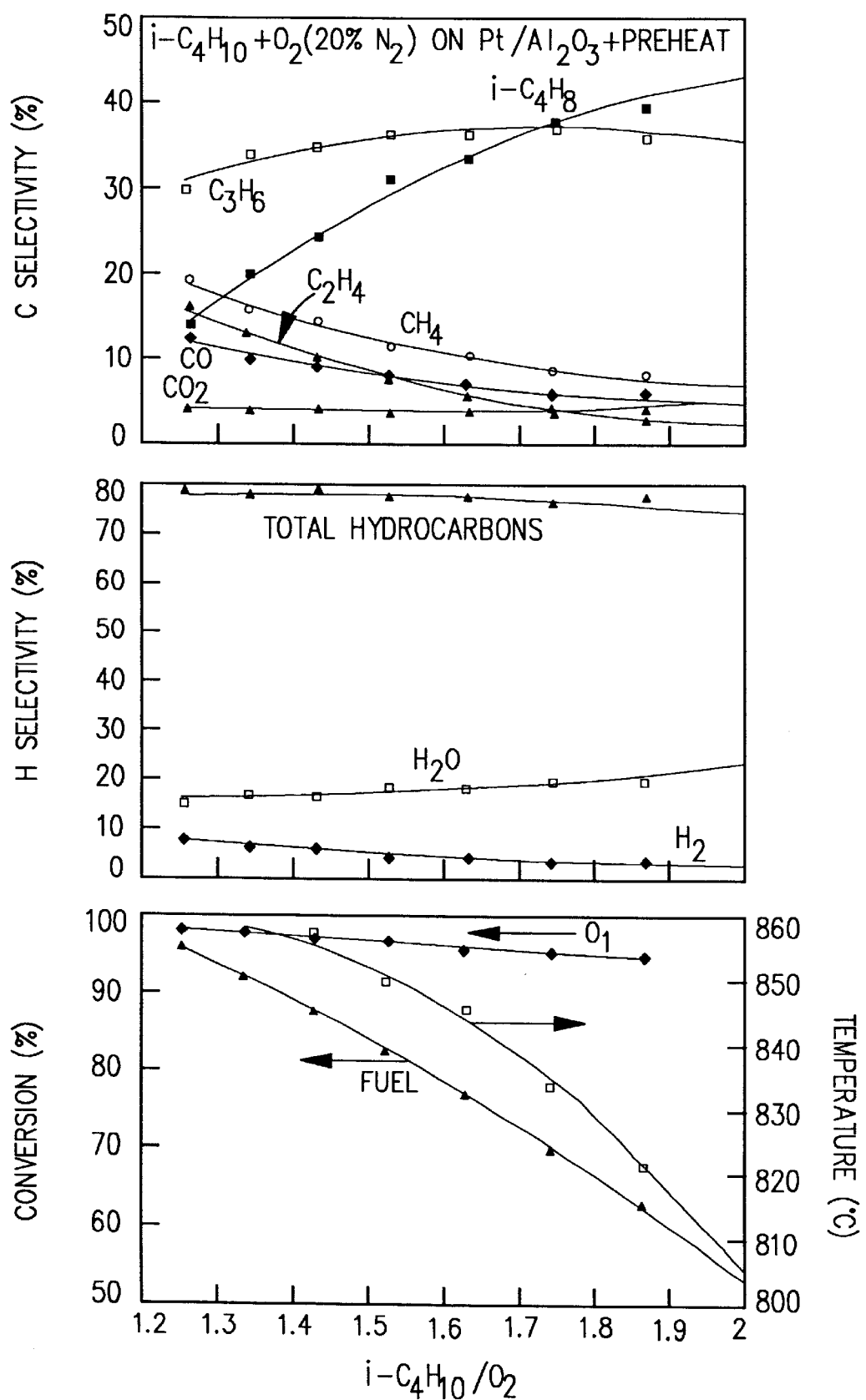
FIG. 10 shows the effect of a reduction in the amount of $N_2$ diluent present in the reactant stream.
Figure 11:
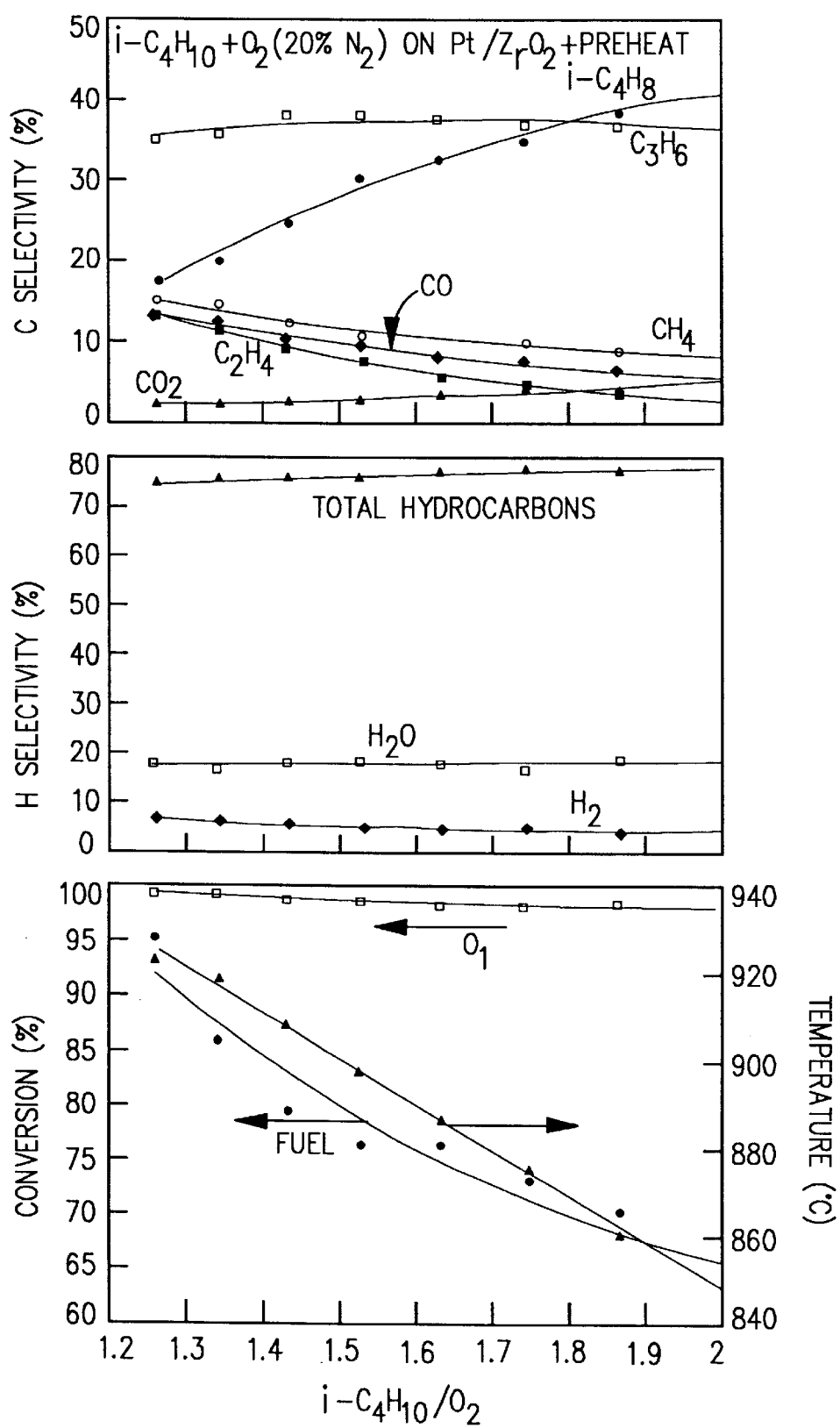
FIG. 11 shows isobutane oxidation in $O_2$ (20% $N_2$) over a 1.8 wt. % Pt/$ZrO_2$ catalysts.

FIG. 10 shows isobutane oxidation in $O_2$ (20% $N_2$) over a 5.1 wt. % $Pt/Al_2O_3$ catalyst. FIG. 11 shows isobutane oxidation in $O_2$ (20% $N_2$) over a 1.8 wt. % $Pt/ZrO_2$ catalyst. The reactants were preheated 360° C. above ambient before reaching the reaction zone. The reaction temperature over the $Pt/ZrO_2$ catalysts is higher than the reaction temperature over the $Pt/Al_2O_3$ catalyst by about 50–80° C. The conversions in FIG. 11 are slightly higher than those shown in FIG. 10. Less $CH_4$ is produced over the $ZrO_2$ support.

TABLE II[1]

| Run | Mole Ratio Isobutane Oxygen | Catalyst[2] | Conversion Mole % | Selectivity Mole % | | | Yield Mole % | | |
|---|---|---|---|---|---|---|---|---|---|
| | | | | Olefins | Isobutene | Propene | Olefins | Isobutene | Propene |
| 1 | 2.00 | A | 52 | 83 | 45 | 36 | 43 | 23 | 19 |
| 2 | 2.00 | B | 62 | 80 | 41 | 36 | 50 | 52 | 22 |
| 3 | 2.00 | C | 55 | 81 | 42 | 36 | 45 | 23 | 20 |
| 4 | 1.43 | A | 75 | 75 | 33 | 36 | 56 | 25 | 27 |
| 5 | 1.43 | B | 87 | 72 | 25 | 38 | 63 | 22 | 33 |
| 6 | 1.43 | C | 85 | 76 | 30 | 38 | 65 | 26 | 33 |

[1]Conditions: oxidation in $O_2$ (20% $N_2$ diluent), total flow rate 5 slpm, 360° C. reactant preheat
[2]A = 5.1 wt % Pt on $Al_2O_3$ monolith; B = 1.8 wt % Pt on $ZrO_2$ monolith; C = 2.6 wt % Pt on $ZrO_2$ monolith.

Example 8

Propane+Air

Figure 6:
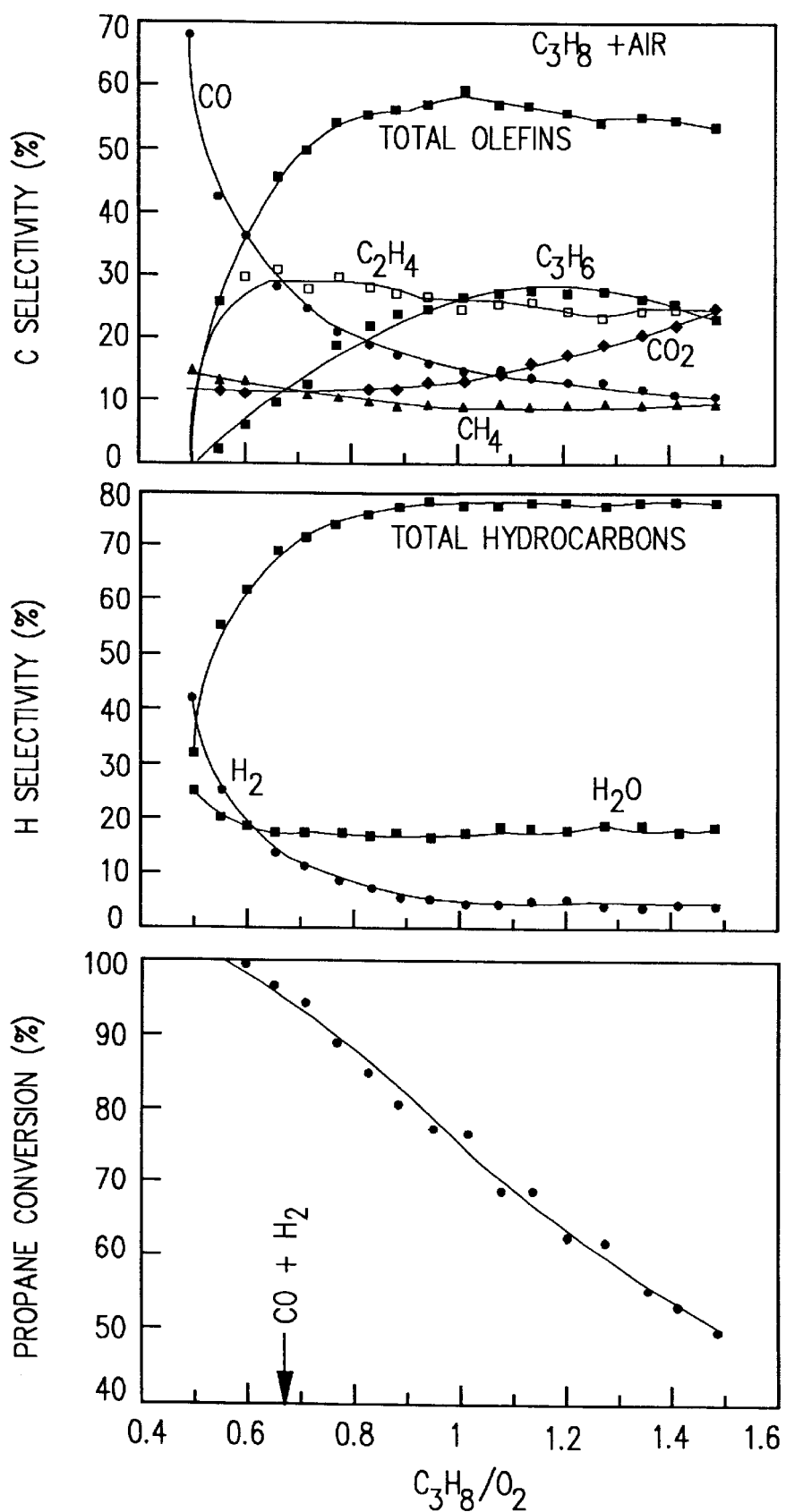
FIG. 6 shows the carbon atom and hydrogen atom selectivities and the propane conversion for the oxidation of propane in air over the 5.1 wt % Pt catalyst as a function of the $C_3H_8/O_2$ ratio in the feed.

FIG. 6 shows the carbon atom and hydrogen atom selectivities and the propane conversion for the oxidation of propane in air over the 5.1 wt % Pt catalyst as a function of the $C_3H_8/O_2$ ratio in the feed. In these runs, the relative amounts of propane and air were varied while maintaining a fixed total flow of 5 SLPM with room temperature feed.

At the stoichiometric composition for the production of synthesis gas ($C_3H_8/O_2$=0.67) the observed selectivity to ethylene was 30%. In fact, at $C_3H_8/O_2$ ratios >0.67, ethylene and propylene are the dominant products. Ethylene selectivity peaks a about 30% at the synthesis gas stoichiometry with a propane conversion >95% and propylene selectivity peaks at about 30% near a $C_3H_8/O_2$ ratio of 1.2 with a propane conversion of about 65%. At $C_3H_8/O_2$ ratios >0.8, the total olefin production ($C_2H_4$, $C_3H_6$, and $C_4H_8$) remains fairly constant with a selectivity of 55–60%. This selectivity peaks near a $C_3H_8/O_2$ ratio of 1.0. This is surprising since thermodynamics predicts the production of only CO, $H_2$, and graphite in this composition and temperature region. Figure A also shows that the ratio of the ethylene selectivity to the methane selectivity is nearly 2:1 on a carbon atom basis. This corresponds to one mole of ethylene formed for every mole of methane and supports the unimolecular cracking reaction.

Example 9

Oxygen Enrichment

Figure 7:
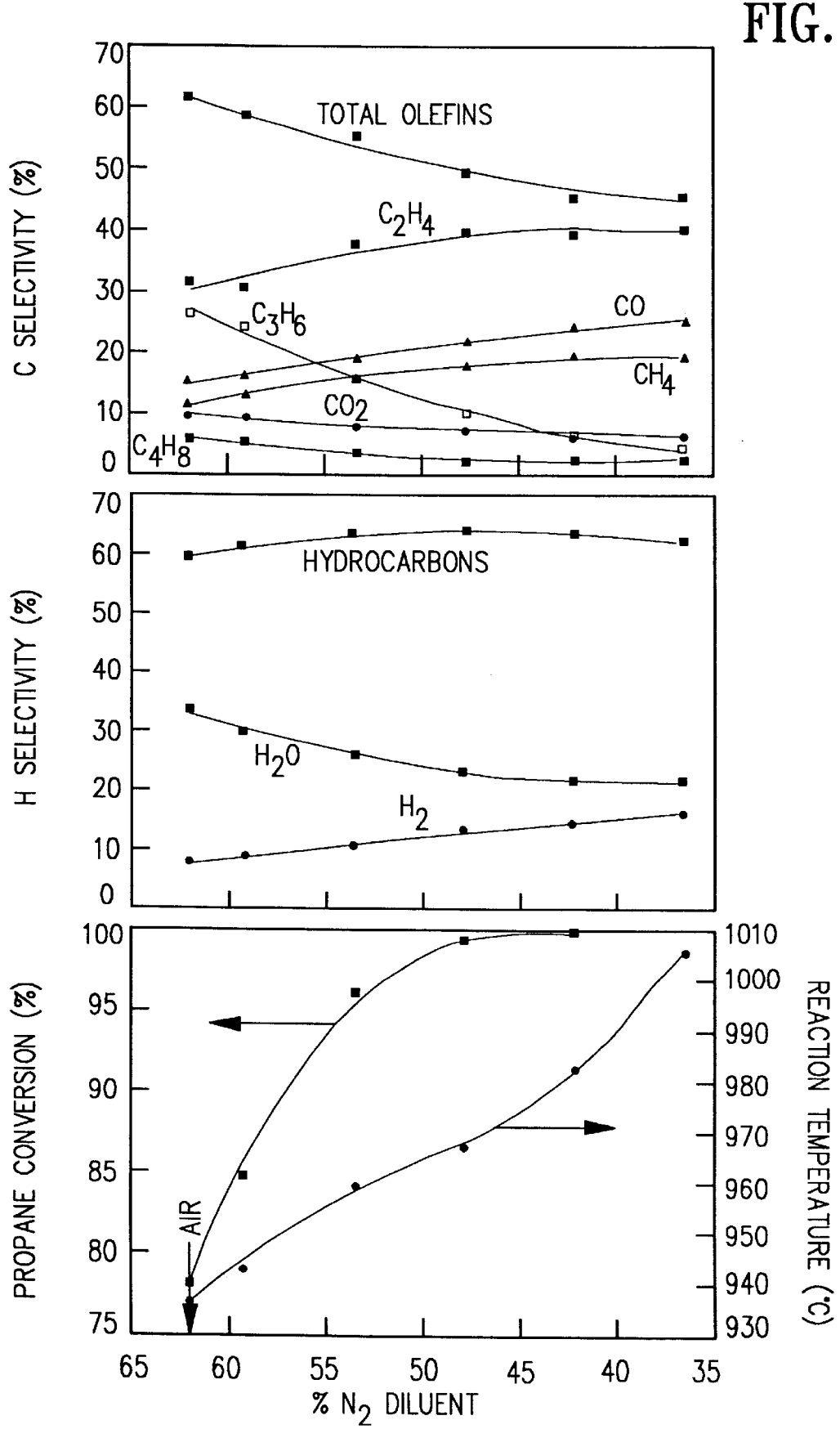
FIG. 7 shows the carbon atom and hydrogen atom selectivities, the propane conversion, and the reaction temperature as the level of dilution decreases.

The optimum olefin yield in air is obtained near a $C_3H_8/O_2$ ratio of 1.0. Runs were conducted at this $C_3H_8/O_2$ ratio to examine the effect of $N_2$ dilution. As shown in FIG. 7, the $N_2$ diluent was decreased from the air composition (62% $N_2$ at a $C_3H_8/O_2$ ratio of 1.0) to 36% $N_2$ diluent (a 1:1 $N_2:O_2$ ratio). The level of $N_2$ dilution was not reduced beyond this point because the reaction temperature increased rapidly with decrease in dilution. Throughout this process, the total flow rate was maintained at 5 SLPM. FIG. 7 shows the carbon atom and hydrogen atom selectivities, the propane conversion, and the reaction temperature as the level of dilution decreases.

There is a large effect due to the diluent. This is primarily because the reaction is autothermal, and reduction in $N_2$ increases the reaction temperature from 940° C. in air to 1010° C. in the most $O_2$ enriched case. At the higher temperature, the propane conversion increases very quickly to 100%. Also, the selectivity to ethylene increases to >40% at complete propane conversion and the selectivity to propylene falls. Although ethylene selectivity improves at the higher temperature associated with the oxygen enriched case, total olefin production is slightly higher at the lower temperatures.

Example 10 n-Butane+$O_2$

Figure 8:
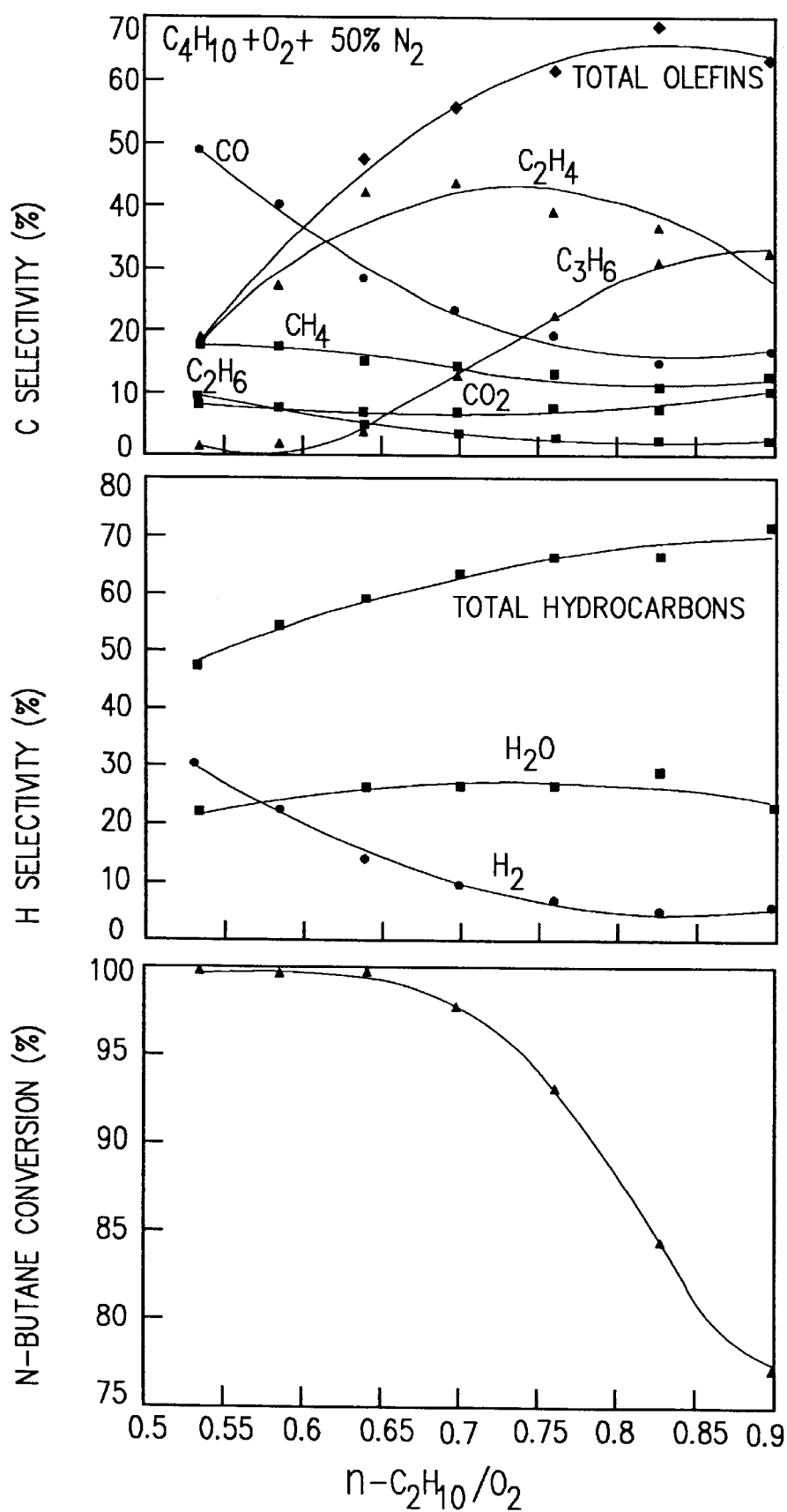
FIG. 8 shows the variation in selectivities and conversion with the n-$C_4H_{10}/O_2$ ratio at a fixed level of 50% $N_2$ dilution.

FIG. 8 illustrates the variation in selectivities and conversion with the n-$C_4H_{10}/O_2$ ratio at a fixed level of 50% $N_2$ dilution. The reactants, n-butane and $O_2$ (50% $N_2$) pass over a 5.1 wt. % Pt/α-$Al_2O_3$ catalyst. Ethylene selectivity peaks near a $C_4H_{10}/O_2$ ratio of 0.7 and reaches >40% at >95% conversion of n-butane. The propylene selectivity increases as the $C_4H_{10}/O_2$ ratio increases.

Example 11 i-Butane+Air

Figure 9:
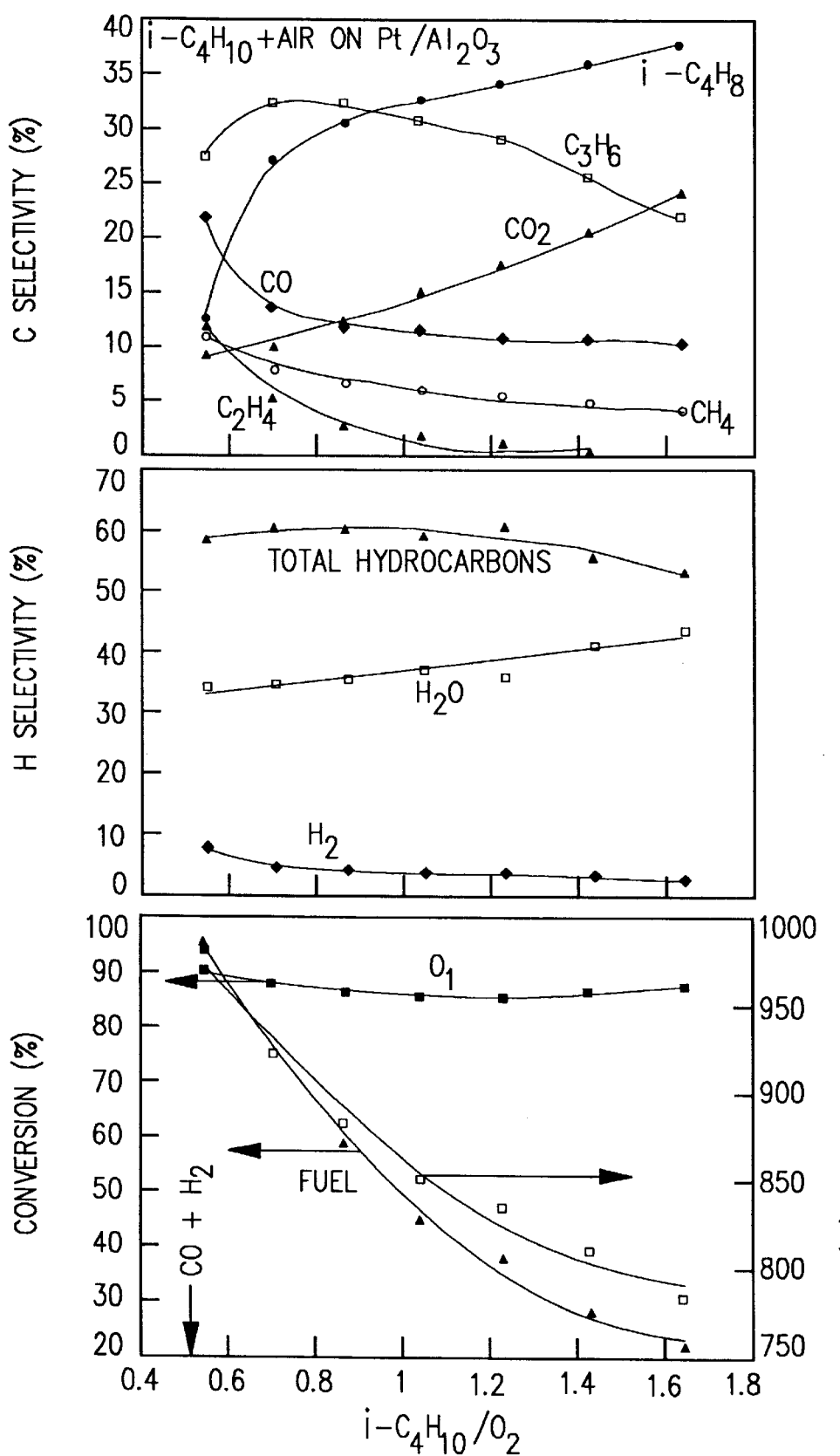
FIG. 9 shows the carbon atom and hydrogen atom selectivities, conversion, and the reaction temperature for the oxidation of isobutane in air over a 5.1 wt. % Pt/α-$AlO_3$ catalysts as a function of the fuel/$O_2$ ratio in the feed.

FIG. 9 shows the carbon atom and hydrogen atom selectivities, conversion, and the reaction temperature for the oxidation of isobutane in air over a 5.1 wt. % Pt/α-$AlO_3$ catalysts as a function of the fuel/$O_2$ ratio in the feed. The relative amounts of isobutane and air were adjusted while maintaining a constant total feed flow rate of 5 SLPM with room temperature feed.

Runs were conducted between the stoichiometric fuel/$O_2$ ratios for the production of syngas and for oxidative dehydrogenation. Runs were not conducted at fuel/$O_2$ ratios less than 0.5 due to the flammability of these mixtures. If only oxidation reactions were occurring, it would be expected that production would shift from CO and $H_2$ at the leaner compositions to isobutylene and $H_2O$ at the richer compositions. FIG. 9 indeed exhibits this trend. The reaction temperature is also near the adiabatic reaction temperatures for these reactions.

Several other reactions, including thermal dehydrogenation and cracking are also taking place. This masks the trend described in the previous paragraph. Syngas production is suppressed in favor of thermal cracking to form $C_3H_6$ and $CH_4$. The production of $CO_2$ also increases at richer compositions. The oxygen is not completely consumed (85–90% $O_2$ conversion), but is present in only small quantities. This remaining $O_2$ may be leading to the higher $CO_2$ selectivities achieved in i-$C_4H_{10}$ oxidation compared to n-$C_4H_{10}$ oxidation.

For isobutane oxidation in air, the production shifts from 33% selectivity to $C_3H_6$ with 80% isobutane conversion at a fuel/$O_2$ ratio of 0.7 to 38% selectivity to i-$C_4H_8$ with only 25% isobutane conversion at a fuel/$O_2$ ratio of 1.65. Throughout this composition region, the total olefin selectivity remains high and fairly constant at about 60%.

Example 12 i-Butane+$O_2$

FIG. 10 shows the effect of a reduction in the amount of $N_2$ diluent present in the reactant stream. The reactants, isobutane and $O_2$ (with 20% $N_2$ present for GC calibration) are preheated to 360° C. prior to reaching the catalytic zone where they pass over a 5.1 wt. % Pt/α-$Al_2O_3$ ceramic foam catalyst. FIG. 10 shows another substantial increase in the isobutane conversion while there is no significant decrease in isobutylene selectivity. At a fuel/$O_2$ ratio of 1.65, the isobutane conversion is now 75% with an isobutylene selectivity of 35%. The $O_2$ conversion has also increased to 95 to 98%. The selectivity to isobutylene is nearly 45% at the stoichiometric ratio of oxidative dehydrogenation (fuel/$O_2$= 2.0) while the conversion is still greater than 50%.

The invention claimed is:

1. A process for the production of a mono-olefin from a gaseous paraffinic hydrocarbon having at least two carbon atoms or mixtures thereof comprising reacting said hydrocarbons and molecular oxygen in the presence of a platinum catalyst consisting essentially of 2 to 90 wt. % platinum on a ceramic foam monolith consisting of the oxides of Zr, Ca, Mg, Hf, Ti or mixtures thereof.

2. The process according to claim 1 wherein the platinum is supported on zirconia monolith.

3. The process according to claim 1 wherein said gaseous paraffin and said oxygen have a flow rate in the range of 60,000 to 10,000,000 hr$^{-1}$ GHSV.

4. The process according to claim 3 wherein said gaseous paraffin and said oxygen have a flow rate in the range of 300,000 to 3,000,000 hr$^{-1}$ GHSV.

5. The process according to claim 1 wherein said gaseous paraffinic hydrocarbon comprises an alkane or mixture of alkanes having two to twenty carbon atoms.

6. The process according to claim 5 wherein said alkane or mixture of alkanes have two to eight carbon atoms.

7. The process according to claim 5 wherein said alkane or mixture of alkanes is ethane, propane, n-butane isobutane, n-pentane, isoamylenes, n-hexane, isohexanes, n-heptane, isoheptane, octane, isooctanes or mixtures thereof.

8. The process according to claim 5 wherein said alkane or mixture of alkanes comprises ethane.

9. The process according to claim 5 wherein said alkane or mixture of alkanes comprises propane.

10. The process according to claim 5 wherein said alkane or mixture of alkanes comprises n-butane.

11. The process according to claim 5 wherein said alkane or mixture of alkanes comprises isobutane.

12. The process according to claim 1 wherein said paraffinic hydrocarbon and molecular oxygen is preheated prior to reacting.

13. The process according to claim 12 wherein said preheating is to a temperature in the range of 25 to 400° C.

14. A process for the production of corresponding olefins, comprising feeding a gaseous alkane or mixture of alkanes having two to twenty carbon atoms and molecular oxygen at a flow rate of 60,000 to 3,000,000 hr$^{-1}$ to a catalyst consisting essentially of 2 to 20 wt % platinum supported on a zirconia monolith.

* * * * *